(12) United States Patent
Berg et al.

(10) Patent No.: US 7,929,129 B2
(45) Date of Patent: Apr. 19, 2011

(54) INSPECTION SYSTEMS FOR GLASS SHEETS

(75) Inventors: David Berg, Rochester, NY (US);
Clarke Kimberly Eastman, Ithaca, NY (US); Jacques Gollier, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/782,832

(22) Filed: May 19, 2010

(65) Prior Publication Data

US 2010/0296084 A1 Nov. 25, 2010

Related U.S. Application Data

(60) Provisional application No. 61/180,469, filed on May 22, 2009.

(51) Int. Cl.
*G01N 21/00* (2006.01)
(52) U.S. Cl. ............... 356/239.1; 356/239.7; 356/237.2
(58) Field of Classification Search ............... 356/239.1, 356/239.7, 237.2
See application file for complete search history.

(56) References Cited

U.S. PATENT DOCUMENTS

| 3,748,015 | A | 7/1973 | Offner .......................... 350/55 |
| 3,951,546 | A | 4/1976 | Markle .......................... 355/51 |
| 5,550,672 | A * | 8/1996 | Cook ............................ 359/365 |
| 6,362,923 | B1 | 3/2002 | Lange et al. .................. 359/689 |
| 6,392,793 | B1 | 5/2002 | Chuang et al. ................ 359/364 |
| 6,801,357 | B2 | 10/2004 | Shafer et al. ................... 1/354 |
| 7,158,215 | B2 | 1/2007 | Harned et al. ................ 355/66 |

FOREIGN PATENT DOCUMENTS

| JP | 2004/037400 | 2/2004 |
| WO | 2004/005902 | 1/2004 |

* cited by examiner

*Primary Examiner* — Roy Punnoose
(74) *Attorney, Agent, or Firm* — Jeffrey A. Schmidt

(57) ABSTRACT

Glass inspection systems are provided for detecting particles and defects in or on a glass sheet or glass ribbon (2, 14). The system is mounted so that the surface (1) to be inspected is in the object plane of a reflective lens (10). The lens images a thin stripe area, long in the direction tangent to the lens circumference and short in the radial direction, onto a linescan camera (18). A line illuminator (12) can be mounted so that it illuminates the stripe area. To perform the inspection, the system is moved with respect to the glass in the direction perpendicular to the long axis of the stripe, either by moving the system over the glass or by moving the glass while the system is fixed. Image information is collected by the linescan camera during this motion and assembled into an image.

19 Claims, 15 Drawing Sheets

INSPECTION SYSTEMS FOR GLASS SHEETS

This application claims the benefit of U.S. Provisional Application Ser. No. 61/180,469, filed May 22, 2009, entitled "Inspection Systems for Glass Sheets".

FIELD

This disclosure relates to the inspection of glass sheets.

DEFINITIONS

As used in the disclosure and the claims, the following terms shall have the following meanings:

"Defects" refers collectively to particles and defects on or in a glass sheet.

"Glass sheet" refers to either an individual piece of glass or a glass ribbon from which individual pieces are separated, depending on the particular application of the inspection system, i.e., whether the system is used to inspect a glass ribbon or individual pieces of glass separated from a ribbon.

"Light" refers generally to electromagnetic radiation and includes radiation in both the visible and non-visible ranges.

"Linescan camera" refers to a detector having a light sensitive area composed of pixels, the length L of the light sensitive area being at least 10 times the width W of the area. Linescan cameras include time delay and integration (TDI) cameras (also known as time domain integration cameras) having L/W ratios greater than 10.

BACKGROUND

The glass sheets used as substrates for display applications, e.g., liquid crystal displays (LCDs) and organic light emitting diode (OLED) displays, need to have surfaces which are essentially free of defects having dimensions on the order of 1 micron and above. Accordingly, extensive efforts have been undertaken to find effective ways of inspecting glass sheets for such defects.

The small sizes of the defects, the fact that glass sheets are transparent at the wavelengths normally used for inspection, and the fact that the glass sheets are thin, e.g., on the order of 0.2 to 1.2 millimeters for display applications, has made inspection a challenging problem. Moreover, as demand for flat panel displays has increased, the number of glass making lines in operation has also increased. As a result, the need for inspection equipment has increased, thus making the cost and complexity of such equipment an important consideration in the evaluation of a system's suitability for this application.

As discussed below, the present disclosure provides inspection systems which can meet the performance criteria associated with the reliable inspection of display glass, while employing relatively inexpensive optical components that can be readily assembled into a compact device that can be easily deployed in a manufacturing setting.

SUMMARY

In accordance with a first aspect, apparatus is disclosed for inspecting a transparent glass sheet having a first surface and a second surface which includes:

(A) a light source which illuminates a portion of the glass sheet;
(B) a linescan camera which detects light scattered from defects on or in the glass sheet, the linescan camera comprising a plurality of pixels which form a light sensitive area having a length L and a width W; and
(C) an optical system that transfers scattered light from defects to the linescan camera, the optical system having a numerical aperture NA and comprising:
  (i) a primary concave mirror having a first portion and a second portion, the mirror having a radius of curvature R; and
  (ii) a convex secondary mirror;
wherein:
  (a) scattered light from a defect reaches the linescan camera by an optical path that includes reflection from the first portion of the concave primary mirror, reflection from the convex secondary mirror, and reflection from the second portion of the concave primary mirror;
  (b) the centers of curvature of the primary and secondary mirrors are substantially coincident and the radius of the secondary mirror is substantially equal to one-half of the radius of the primary mirror; and
  (c) L, W, and R satisfy the relationships:

$L/R \leq 0.25$; and $W/R \leq 0.14*(\text{sqrt}(1-(L/R)^2)-1)+0.046$ for $NA \geq 0.10$; and $W/R \leq 0.14*(\text{sqrt}(1-(L/R)^2)-1)+0.033$ for $NA \geq 0.12$; and $W/R \leq 0.14*(\text{sqrt}(1-(L/R)^2)-1)+0.020$ for $NA \geq 0.15$.

In accordance with a second aspect, apparatus is disclosed for inspecting a transparent glass sheet having a first surface and a second surface which includes:

(A) a light source which illuminates a portion of the glass sheet;
(B) a linescan camera which detects light scattered from defects on or in the glass sheet, the linescan camera comprising a plurality of pixels which form a light sensitive area having a length L and a width W; and
(C) an optical system that transfers scattered light from defects to the linescan camera, the optical system having a numerical aperture NA and comprising:
  (i) a primary concave mirror having a first portion and a second portion, the mirror having a radius of curvature R; and
  (ii) a convex secondary mirror;
wherein:
  (a) scattered light from a defect reaches the linescan camera by an optical path that includes reflection from the first portion of the concave primary mirror, reflection from the convex secondary mirror, and reflection from the second portion of the concave primary mirror;
  (b) the centers of curvature of the primary and secondary mirrors are substantially coincident and the radius of the secondary mirror is substantially equal to one-half of the radius of the primary mirror; and
  (c) the optical system when focused on a first surface of the glass sheet has a point spread function of semi-diameter D1 at that surface and has a point spread function of semi-diameter D2 at the second surface, where D1 and D2 satisfy the relationship:

$D2/D1 \geq 35$ for a glass sheet having a thickness in the range of 0.2 to 1.2 millimeters.

In accordance with a third aspect, a method is disclosed for detecting a defect on or in a transparent glass sheet having a first surface and a second surface which includes:

(A) illuminating a portion of the glass sheet;
(B) transferring light scattered by a defect from the glass sheet to a linescan camera using an optical system having a numerical aperture NA and comprising:
  (i) a primary concave mirror having a first portion and a second portion, the mirror having a radius of curvature R; and
  (ii) a convex secondary mirror; and
(C) providing relative motion between the glass sheet and the linescan camera (e.g., by translating the glass sheet relative to the linescan camera);
wherein:
(a) scattered light from a defect reaches the linescan camera by an optical path that includes reflection from the first portion of the concave primary mirror, reflection from the convex secondary mirror, and reflection from the second portion of the concave primary mirror;
(b) the centers of curvature of the primary and secondary mirrors are substantially coincident and the radius of the secondary mirror is substantially equal to one-half of the radius of the primary mirror;
(c) the linescan camera comprises a plurality of pixels which form a light sensitive area having a length L and a width W; and
(d) L, W, and R satisfy the relationships:

$$L/R \leq 0.25; \text{ and}$$

$$W/R \leq 0.14*(\text{sqrt}(1-(L/R)^2)-1)+0.046 \text{ for } NA \geq 0.10; \text{ and}$$

$$W/R \leq 0.14*(\text{sqrt}(1-(L/R)^2)-1)+0.033 \text{ for } NA \geq 0.12; \text{ and}$$

$$W/R \leq 0.14*(\text{sqrt}(1-(L/R)^2)-1)+0.020 \text{ for } NA \geq 0.15.$$

In certain embodiments, the apparatus of the first and second aspects and/or the method of the third aspect has some or all of the following features:
(a) an optical system whose NA satisfies the relationship:

$$0.10 \leq NA \leq 0.15;$$

(b) an optical system that has 1:1 magnification;
(c) an optical system whose aperture stop is located at the secondary mirror;
(d) a pixel size for the linescan camera that is in the range of 5 to 20 microns;
(e) an optical path that includes only reflective optical surfaces;
(f) an optical system that is substantially telecentric in object space such that the variation in image size is less than the size of a pixel of the linescan camera over the optical system's depth of field;
(g) an optical system whose field curvature is less than the optical system's depth of field;
(h) an optical system whose geometric distortion is less than 1% over the length L of the light sensitive area of the linescan camera; and/or
(i) a focusing mechanism which adjusts at least one of (1) the optical path length between the glass sheet and the first portion of the primary concave mirror, and (2) the optical path length between the second portion of the primary concave mirror and the linescan camera.

It is to be understood that both the foregoing general description and the following detailed description are merely exemplary of the invention and are intended to provide an overview or framework for understanding the nature and character of the invention. Additional features and advantages of the invention are set forth in the detailed description which follows, and in part will be readily apparent to those skilled in the art from that description or recognized by practicing embodiments of the invention as described herein. The accompanying drawings are included to provide a further understanding of the invention, and are incorporated in and constitute a part of this specification. It is to be understood that the various features of the invention disclosed in this specification and in the drawings can be used in any and all combinations. By way of non-limiting example, the various features of the embodiments may be combined as set forth in the following aspects.

According to a first aspect, there is provided an apparatus for inspecting a transparent glass sheet having a first surface and a second surface, the apparatus comprising:
(A) a light source which illuminates a portion of the glass sheet;
(B) a linescan camera which detects light scattered from defects on or in the glass sheet, the linescan camera comprising a plurality of pixels which form a light sensitive area having a length L and a width W; and
(C) an optical system that transfers scattered light from defects to the linescan camera, the optical system having a numerical aperture NA and comprising:
  (i) a primary concave mirror having a first portion and a second portion, the mirror having a radius of curvature R; and
  (ii) a convex secondary mirror;
wherein:
(a) scattered light from a defect reaches the linescan camera by an optical path that includes reflection from the first portion of the concave primary mirror, reflection from the convex secondary mirror, and reflection from the second portion of the concave primary mirror;
(b) the centers of curvature of the primary and secondary mirrors are substantially coincident and the radius of the secondary mirror is substantially equal to one-half of the radius of the primary mirror; and
(c) L, W, and R satisfy the relationships:

$$L/R \leq 0.25; \text{ and}$$

$$W/R \leq 0.14*(\text{sqrt}(1-(L/R)^2)-1)+0.046 \text{ for } NA \geq 0.10; \text{ and}$$

$$W/R \leq 0.14*(\text{sqrt}(1-(L/R)^2)-1)+0.033 \text{ for } NA \geq 0.12; \text{ and}$$

$$W/R \leq 0.14*(\text{sqrt}(1-(L/R)^2)-1)+0.020 \text{ for } NA \geq 0.15.$$

According to a second aspect, there is provided the apparatus of Aspect 1 wherein the optical system when focused on the first surface of the glass sheet has a point spread function of semi-diameter D1 at that surface and has a point spread function of semi-diameter D2 at the second surface, where D1 and D2 satisfy the relationship:

$$D2/D1 \geq 35$$

for a glass sheet having a thickness in the range of 0.2 to 1.2 millimeters.

According to a third aspect, there is provided an apparatus for inspecting a transparent glass sheet having a first surface and a second surface, the apparatus comprising:
(A) a light source which illuminates a portion of the glass sheet;
(B) a linescan camera which detects light scattered from defects on or in the glass sheet, the linescan camera comprising a plurality of pixels which form a light sensitive area having a length L and a width W; and (C) an optical system that transfers scattered light from defects to the linescan camera, the optical system having a numerical aperture NA and comprising:
  (i) a primary concave mirror having a first portion and a second portion, the mirror having a radius of curvature R; and
  (ii) a convex secondary mirror;
wherein:
  (a) scattered light from a defect reaches the linescan camera by an optical path that includes reflection from the first portion of the concave primary mirror, reflection from the convex secondary mirror, and reflection from the second portion of the concave primary mirror;
  (b) the centers of curvature of the primary and secondary mirrors are substantially coincident and the radius of the secondary mirror is substantially equal to one-half of the radius of the primary mirror; and
  (c) the optical system when focused on a first surface of the glass sheet has a point spread function of semi-diameter D1 at that surface and has a point spread function of semi-diameter D2 at the second surface, where D1 and D2 satisfy the relationship:

$$D2/D1 \geq 35$$

for a glass sheet having a thickness in the range of 0.2 to 1.2 millimeters.

According to a fourth aspect, there is provided the apparatus of any one of Aspects 1, 2, or 3 wherein NA satisfies the relationship:

$$0.10 \leq NA \leq 0.15.$$

According to a fifth aspect, there is provided the apparatus of any one of Aspects 1-4 wherein the optical system has 1:1 magnification.

According to a sixth aspect, there is provided the apparatus of any one of Aspects 1-5 wherein the optical system's aperture stop is located at the secondary mirror.

According to a seventh aspect, there is provided the apparatus of any one of Aspects 1-6 wherein the pixel size of the linescan camera is in the range of 5 to 20 microns According to an eighth aspect, there is provided the apparatus of any one of Aspects 1-7 wherein the optical path includes only reflective optical surfaces.

According to a ninth aspect, there is provided the apparatus of any one of Aspects 1-8 wherein the optical system is substantially telecentric in object space such that the variation in image size is less than the size of a pixel of the linescan camera over the optical system's depth of field.

According to a tenth aspect, there is provided the apparatus of any one of Aspects 1-9 wherein the optical system's field curvature is less than the optical system's depth of field.

According to an eleventh aspect, there is provided the apparatus of any one of Aspects 1-10 wherein the optical system's geometric distortion is less than 1% over the length L of the light sensitive area of the linescan camera.

According to a twelfth aspect, there is provided the apparatus of any one of Aspects 1-11 further comprising a focusing mechanism which adjusts at least one of:
  (i) the optical path length between the glass sheet and the first portion of the primary concave mirror object; and
  (ii) the optical path length between the second portion of the primary concave mirror object and the linescan camera.

According to a thirteenth aspect, there is provided a method of detecting a defect on or in a transparent glass sheet having a first surface and a second surface, the method comprising:

(A) illuminating a portion of the glass sheet;
  (B) transferring light scattered by a defect from the glass sheet to a linescan camera using an optical system having a numerical aperture NA and comprising:
    (i) a primary concave mirror having a first portion and a second portion, the mirror having a radius of curvature R; and
    (ii) a convex secondary mirror; and
  (C) providing relative motion between the glass sheet and the linescan camera;
wherein:
  (a) scattered light from a defect reaches the linescan camera by an optical path that includes reflection from the first portion of the concave primary mirror, reflection from the convex secondary mirror, and reflection from the second portion of the concave primary mirror;
  (b) the centers of curvature of the primary and secondary mirrors are substantially coincident and the radius of the secondary mirror is substantially equal to one-half of the radius of the primary mirror;
  (c) the linescan camera comprises a plurality of pixels which form a light sensitive area having a length L and a width W; and
  (d) L, W, and R satisfy the relationships:

$$L/R \leq 0.25; \text{ and}$$

$$W/R \leq 0.14*(\mathrm{sqrt}(1-(L/R)^2)-1)+0.046 \text{ for } NA \geq 0.10; \text{ and}$$

$$W/R \leq 0.14*(\mathrm{sqrt}(1-(L/R)^2)-1)+0.033 \text{ for } NA \geq 0.12; \text{ and}$$

$$W/R \leq 0.14*(\mathrm{sqrt}(1-(L/R)^2)-1)+0.020 \text{ for } NA \geq 0.15.$$

According to a fourteenth aspect, there is provided the method of Aspect 13 wherein the optical system when focused on the first surface of the glass sheet has a point spread function of semi-diameter D1 at that surface and has a point spread function of semi-diameter D2 at the second surface, where D1 and D2 satisfy the relationship:

$$D2/D1 \geq 35$$

for a glass sheet having a thickness in the range of 0.2 to 1.2 millimeters.

According to a fifteenth aspect, there is provided the method of Aspect 13 or Aspect 14, further comprising focusing an image of the glass sheet on the linescan camera by adjusting at least one of:
  (i) the optical path length between the glass sheet and the first portion of the primary concave mirror; and
  (ii) the optical path length between the second portion of the primary concave mirror and the linescan camera.

According to a sixteenth aspect, there is provided the method of any one of Aspects 13-15 wherein the optical system is substantially telecentric in object space such that the variation in image size is less than the size of a pixel of the linescan camera over the optical system's depth of field.

According to a seventeenth aspect, there is provided the method of any one of Aspects 13-16 wherein the optical system's field curvature is less than the optical system's depth of field.

According to an eighteenth aspect, there is provided the method of any one of Aspects 13-17 wherein the optical system's geometric distortion is less than 1% over the length of the light sensitive area of the linescan camera.

DETAILED DESCRIPTION

Figure 1:
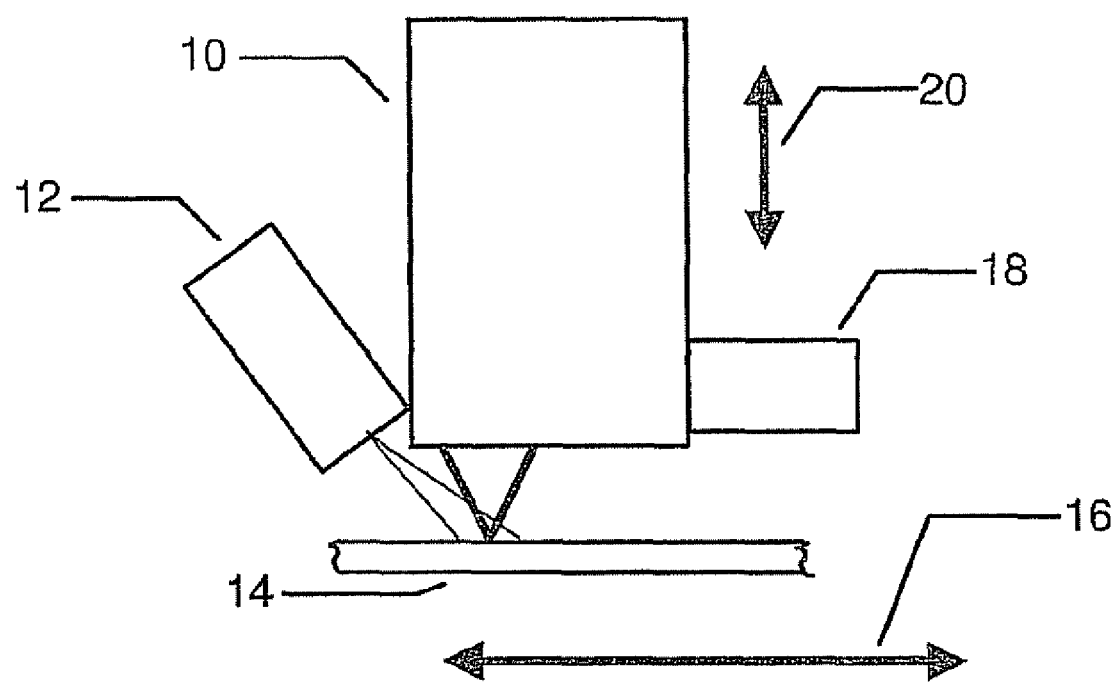
FIG. 1 is a schematic diagram showing components and motions of an embodiment of an inspection system of the present disclosure.

As discussed above, the present disclosure relates to the inspection of glass sheets and, in one application, to the inspection of display glass, either in the form of individual sheets or in the form of the glass ribbon from which the sheets are separated.

Inspection for defects is routinely performed during the manufacture of display glass. Importantly, such glass has two sides (the "A" side and the "B" side) on which defects need to be sensed separately. To sense the defects, the display glass is imaged by a camera system that records light scattered from the defects. In some cases, the entire area of the glass is inspected; in other cases, one or more zones of the glass area are sensed and used as an audit sample.

Because large areas of glass need to be inspected quickly, a linescan camera is used to sense the defects. Such cameras have a long field of view in one dimension (e.g., 27 mm) and a narrow field in the orthogonal direction (e.g., 1.3 mm) For ease of processing (analysis), a defect sensed anywhere on the long axis of the field of view preferably produces a substantially identical pattern on the sensor.

To facilitate effective inspection, in certain embodiments, the inspection systems disclosed herein have the following characteristics:

(a) a field of view (FOV) as long as the length L of the light sensitive area of the linescan camera;
(b) a sufficiently high resolution to sense small defects;
(c) a large numerical aperture (NA) to see weakly scattering defects;
(d) a depth of field (DOF) sufficiently small so that defects from the A and B sides of the glass sheet may be distinguished, i.e., a DOF smaller than the thickness of the glass sheet being viewed;
(e) a substantially flat field so that the surface of the glass sheet remains in focus across the FOV;
(f) color correction so that light sources of different wavelengths may be used;
(g) manufacturability at reasonable cost; and
(h) the ability to collect light from the same group of angles symmetric about a normal to the glass sheet regardless of the defect's position.

In terms of optical terminology, the last of these characteristics corresponds to the inspection system or, more precisely, the lens portion of the inspection system being telecentric or substantially telecentric on the object side, i.e., the entrance pupil of the lens is at a long distance from the elements making up the lens so that the principal rays on the object side are substantially parallel to the lens' optical axis, e.g., the included angle between the principal rays and the optical axis is less than 0.5°. Telecentricity or substantial telecentricity also means that the magnification of the lens does not vary or does not vary substantially with object distance.

Historically, inspection systems have used lenses composed of multiple refractive lens elements. Such lenses have been unable to provide all of the above characteristics. For example, some systems based on refractive technology have had too large a DOF to distinguish A and B side defects. Also, many refractive lenses used in inspection applications did not have sufficiently flat fields, so that defects near the edges of the FOV were focused differently from those near the center. As a result, such systems were not able to distinguish A side and B side defects consistently. In addition, by their nature, refractive lenses are color corrected at best for a limited range of wavelengths. Importantly, in terms of cost, color-corrected, refractive telecentric lenses with large fields of view and sufficiently flat fields are notoriously complex, composed of at least one very large lens element, and expensive.

In accordance with the present disclosure, a lens system based on reflection, rather than refraction, is used to form an image on a linescan camera of a portion of the surface of a glass sheet. As discussed in detail below (see, for example, FIG. 9), the reflective lens system has a structure and optical properties which are strongly linked to the characteristics of the linescan camera, so that these two components work together to provide a level of performance not achievable with refractive systems at any reasonable cost.

A representative structure for an inspection system employing a reflective lens 10 of the type disclosed herein is shown in FIG. 1. As shown in this figure, in addition to the reflective lens 10 and a linescan camera 18, the system normally includes an illuminator 12 for illuminating a portion of the glass sheet, a focusing system for focusing 20 the image of the glass surface onto the light sensitive surface of the linescan camera 18, and a translator for producing relative motion (lateral motion 16) between the glass sheet and the lens/camera assembly. Typically, the relative motion is achieved by translating the glass sheet while holding the lens/camera assembly stationary, although the opposite arrangement or a combination of sheet motion and lens/camera motion can be used if desired. In the case of a continuously moving glass ribbon, the motion of the ribbon can be used to provide some or all of the relative motion between the sheet and the lens/camera assembly.

Figure 2:
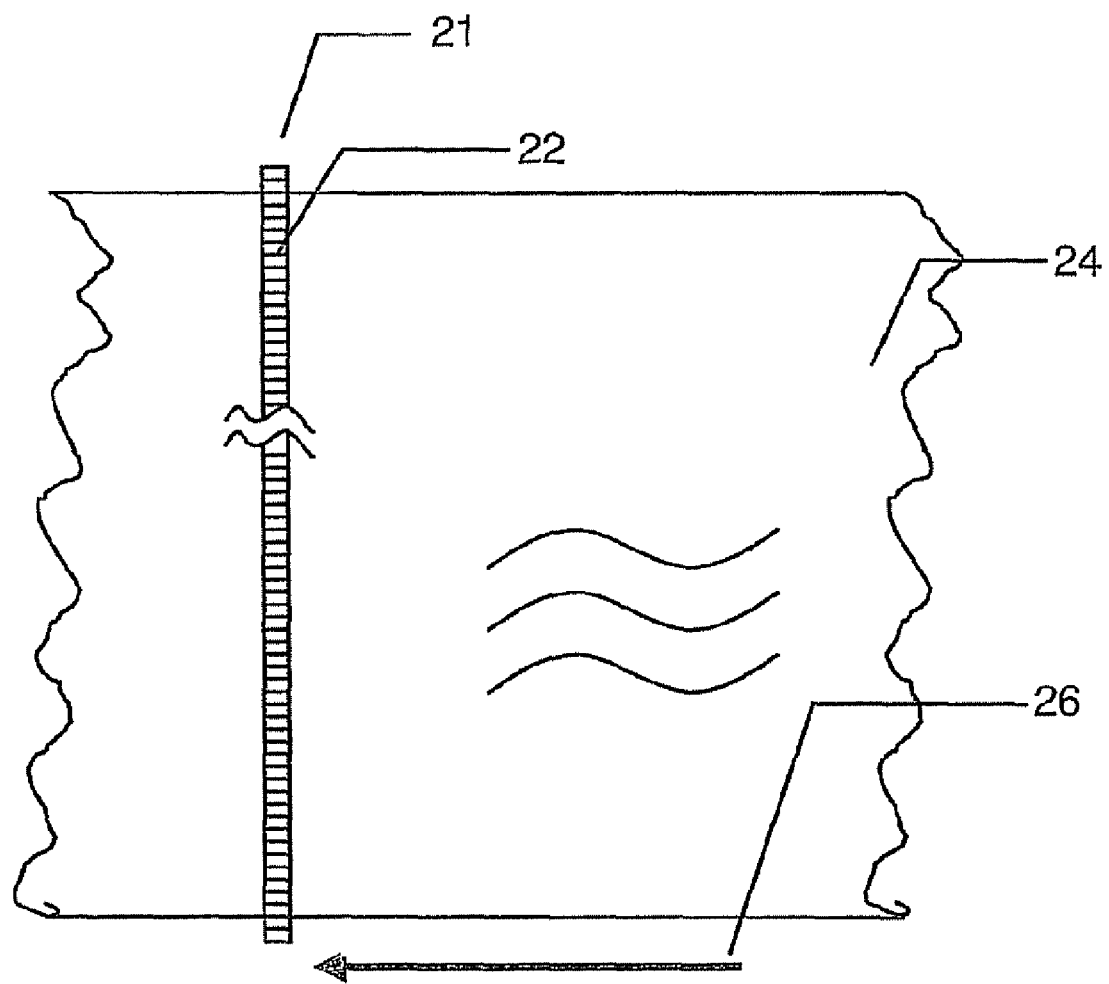
FIG. 2 is a schematic diagram illustrating a mode of operation of a linescan camera.

FIG. 2 illustrates the relative motion in more detail. In particular, this figure illustrates how the relative motion 26 produces an image of a glass surface 24 that moves past the sensor pixels 22 of a linescan sensor 21, thus allowing the camera to produce a digital output indicative of the level of scattered light reaching each pixel as a function of time. The use of a linescan sensor 21, especially the TDI form of this camera, provides the advantage that large amounts of image information can be collected quickly. However, the linescan camera has the disadvantage that its shape is very long in the direction across the image motion and very short in the direction along image motion. This rectangular shape poses an imaging challenge, which the present disclosure overcomes through the use of the reflective lenses discussed generally above and in more detail below.

As known in the art, in the case of a TDI linescan camera, the camera includes an array of pixels, with the rows of the array oriented parallel to the direction of relative motion and the columns orthogonal to that direction. As also known in the art, for such a camera, the collection of light by each member of a row is synchronized with the relative motion between the camera and the image to be recorded, and the charge accumulated by the pixels as a result of exposure to incident light is cyclically integrated from column to column. In this way, the sensitivity of the camera to light from an object which is in motion relative to the camera is substantially increased compared to the sensitivity of a single column of pixels.

As noted above, linescan cameras have a field of view that is large in one direction. Linescan sensors can be extremely narrow (1 pixel for a conventional sensor), or relatively narrow (e.g. 96 pixels in the case of one commercially available TDI sensor) in the other direction. In either case, the ratio between sensor length in the two directions is greater than 10.

Linescan cameras (sensors) used for particle detection typically have pixels in the 5 μm-20 μm range in linear dimension. Defects, e.g., particles, of these diameters can be detected optically. Thus a lens of unity magnification that provides a way to directly relay images of such defects onto a linescan sensor provides a means to inspect large areas with sufficient sensitivity for particles in this size range. Sensors are also routinely used to detect defects considerably smaller than a pixel using sub-pixel resolution techniques. An example of such a technique is to infer a defect's size by the amount of light reflected or scattered. This approach can be used to extend the range of detectable particles to sizes much smaller than a detector pixel while retaining the ability to inspect large areas with sufficient sensitivity. In either case, as discussed below, the reflective lenses of the inspection systems disclosed herein provide sufficient image quality at unity magnification to detect defects of these types. More particularly, the reflective lenses provide image-side resolution at least similar to the sensor pixel size so that the image is sensor limited. Also, the lenses have relatively small f-numbers (relatively large numerical apertures) to gather sufficient light during the short exposure time allotted to each line.

Figure 3:
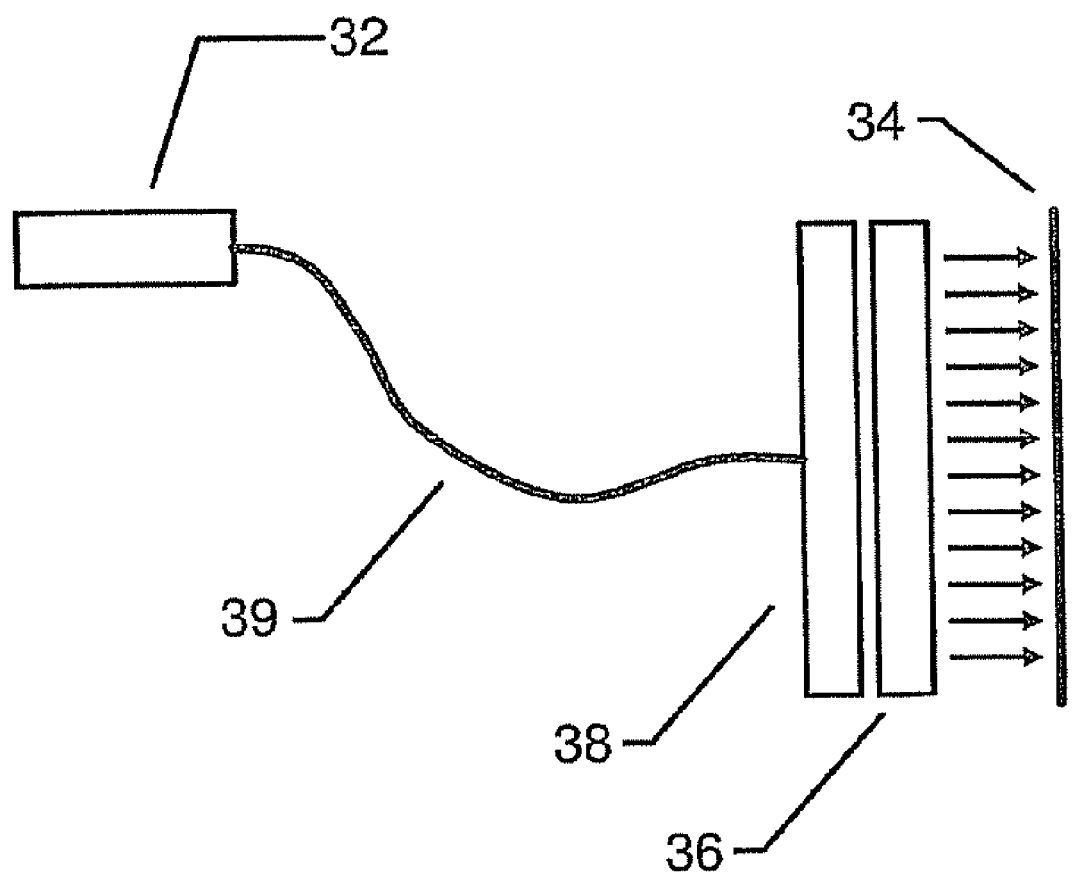
FIG. 3 is a schematic diagram of an embodiment of an illuminator.

FIG. 3 illustrates an embodiment of equipment that can be employed as the illuminator 12 of FIG. 1. As shown in this figure, the illuminator can include a light source 32, e.g., a laser light source operating in the IR range, a fiber optic line light 38 connected to the light source 32 by a fiber optic bundle 39, and a cylindrical condenser lens 36 which produces an illuminated line 34 at the glass sheet. Other equipment can, of course, be used for the illuminator 12. Also, although focused illumination is preferred, diffuse illumination may be suitable for some applications.

Figure 4:
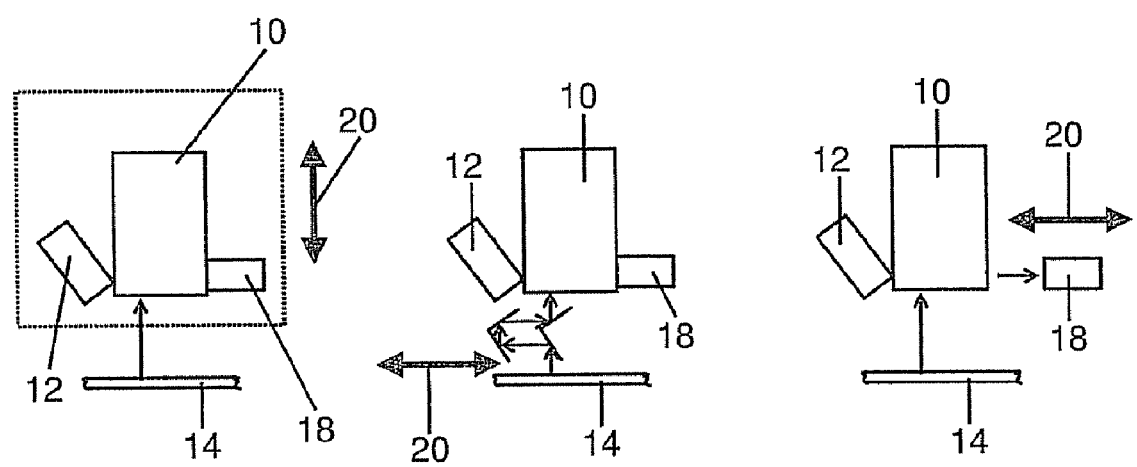
FIG. 4 is a schematic diagram illustrating various approaches for focusing an image of a surface of a glass sheet on a linescan camera. In particular, the left-hand panel illustrates adjusting the lens/camera/illuminator-to-surface distance, the middle panel illustrates adjusting the optical path from the surface to the lens using a "trombone" mirror assembly, and the right hand panel illustrates adjusting the lens to camera sensor distance.

FIG. 4 illustrates representative approaches for focusing an image of a surface of a glass sheet 14, e.g., the side A surface, on the light sensitive area of a linescan camera 18. The left hand panel of FIG. 4 illustrates moving 20 the entire inspection assembly (illuminator 12, lens 10, and camera 18) relative to the glass sheet, while the center panel illustrates the use of a moving 20 mirror assembly, specifically, a "trombone" set of mirrors in this embodiment, to change the optical path length from the glass sheet 14 (the object) to the lens. The use of a moving mirror assembly is facilitated by the relatively long working distance provided by the reflective lenses of the present disclosure. The right hand panel of FIG. 4 illustrates adjusting 20 the lens-to-linescan camera 18 distance to change focus. Again, the reflective lenses of the present disclosure facilitate this approach, in this case through the lens' relatively long back working distance. Rather than physically moving the linescan camera 18, a moving mirror assembly, e.g., a trombone assembly of the type shown in the middle panel, can be used to change the optical distance between the lens and the linescan camera 18 if desired.

It should be noted that if desired both surfaces of a glass sheet 14 can be inspected at the same time by using a beam splitter to split the image beam along with two linescan cameras 18, one focused on one of the sheet's surfaces (e.g., the A side) and the other on the opposite surface (e.g., the B side).

Figure 5:
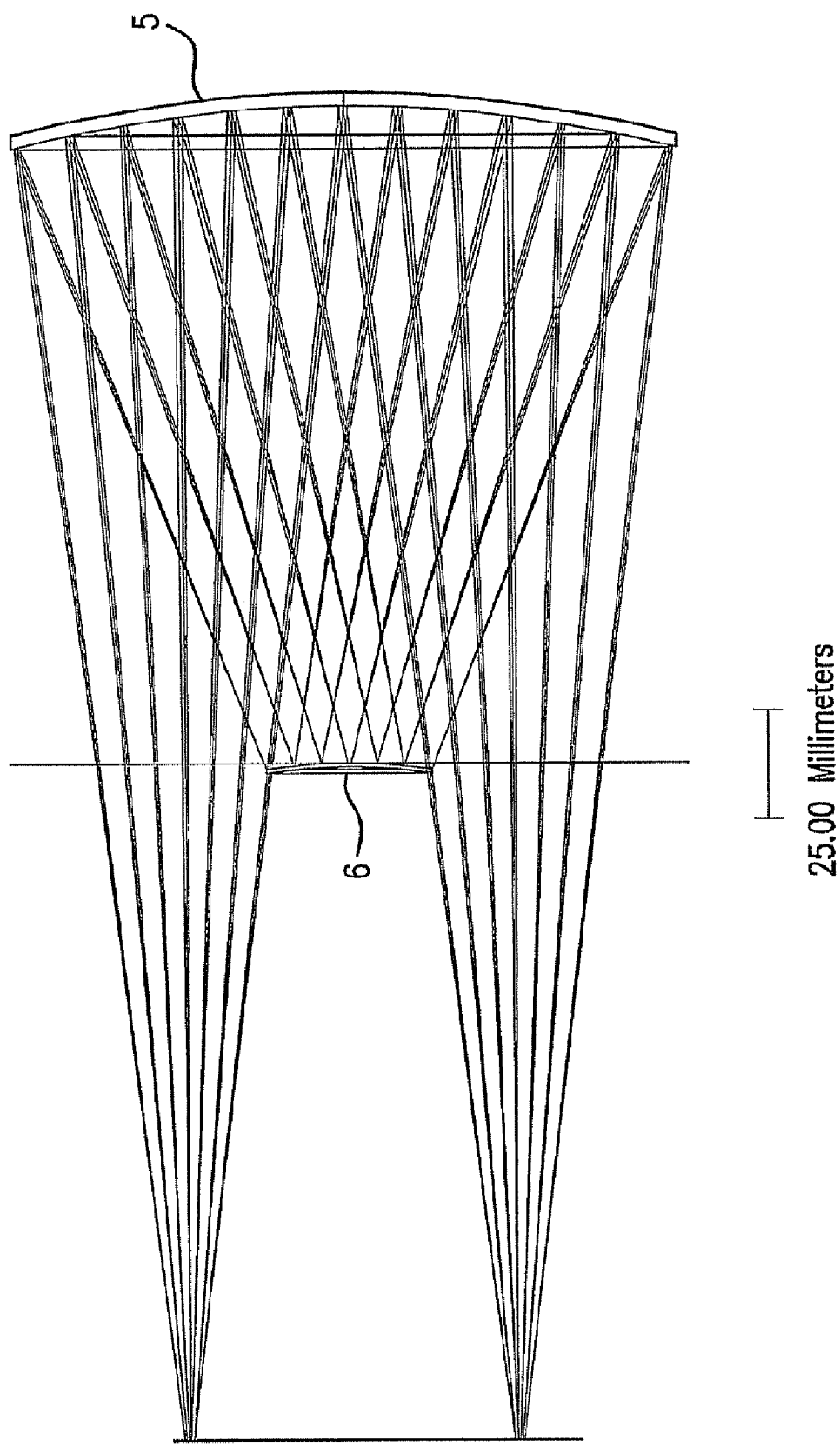
FIG. 5 is a ray tracing for an embodiment of a substantially telecentric reflective lens employing two reflective spherical elements.
Figure 6:
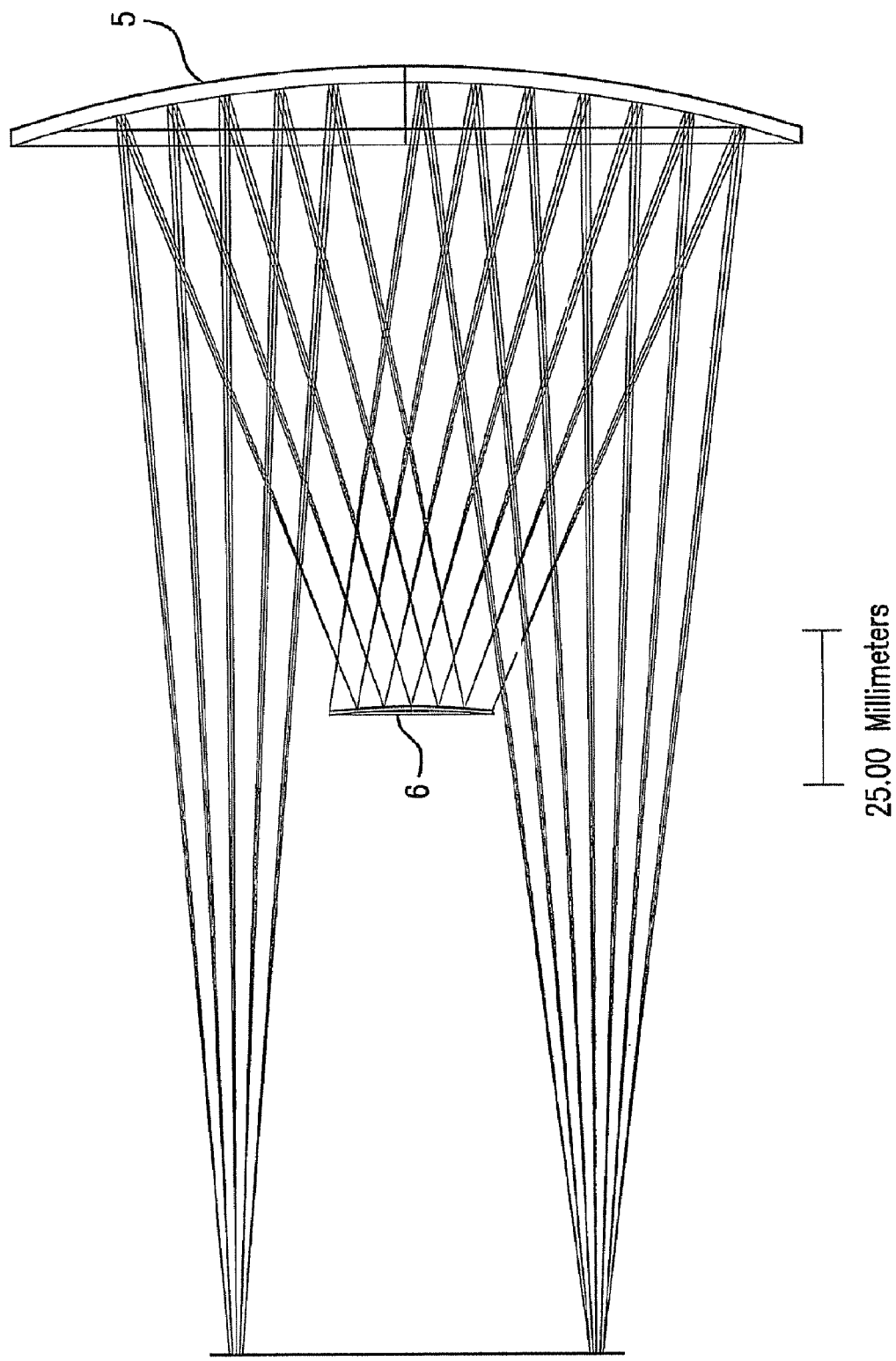
FIG. 6 is a ray tracing for an embodiment of a substantially telecentric reflective lens employing two reflective spherical elements.

FIGS. 5 and 6 show representative examples of reflective lenses that can be used in the inspection systems of the present disclosure. In general terms, these lenses are of the form disclosed in U.S. Pat. No. 3,748,015, the contents of which are incorporated herein by reference in their entirety. Each lens includes a concave primary mirror 5 (large mirror at the right hand side of the figure) and a convex secondary mirror 6 (smaller mirror at the center of the figure). The centers of curvature of the primary 5 and secondary 6 mirrors are coincident or substantially coincident and the radius of the secondary mirror 6 is equal or substantially equal to one-half the radius of the primary mirror 5. Prescriptions for the two lenses are set forth in Table 1, where the dimensions are in millimeters and the designation "Large" refers to the FIG. 5 lens and the designation "Small" refers to the FIG. 6 lens.

The lens forms of these figures exceed the performance of current refractive lens solutions for inspecting each surface of a glass sheet. These lenses have a flat field of view, so that all defects that lie on one plane surface of the glass sheet are equally in focus, and those that lie on the opposite surface are equally out of focus, regardless of their position in the lens' field of view. This allows easy distinction of defects on one surface—say the A side—from those on another surface—say the B side. Refractive lenses have inherently curved focal planes, which must be approximately corrected by balancing positive and negative curvatures in the optical design.

Figure 7:
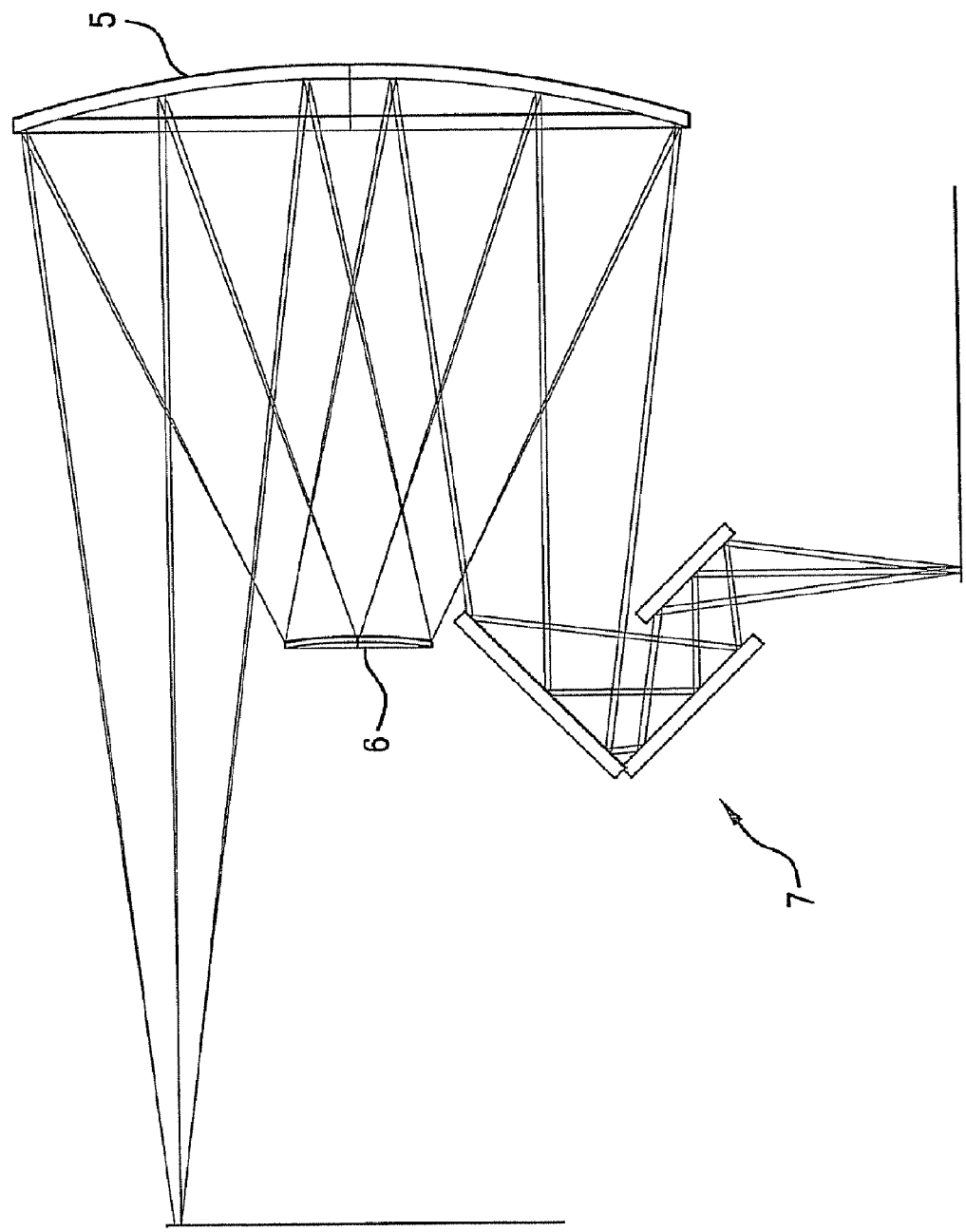
FIG. 7 is a ray tracing for an embodiment of a substantially telecentric reflective lens employing two reflective spherical elements and a mirror assembly for changing the orientation of the lens' object or image plane.

In FIGS. 5 and 6, the object and image planes are shown to be coplanar. For many applications, it will be more convenient to have the object and image planes orthogonal to one another. Such an orientation can be achieved by using one or more turning mirrors. FIG. 7 illustrates an embodiment using three turning mirrors 7 arranged in a trombone configuration that can be used both for orienting the object or image plane and for focusing.

Figure 8:
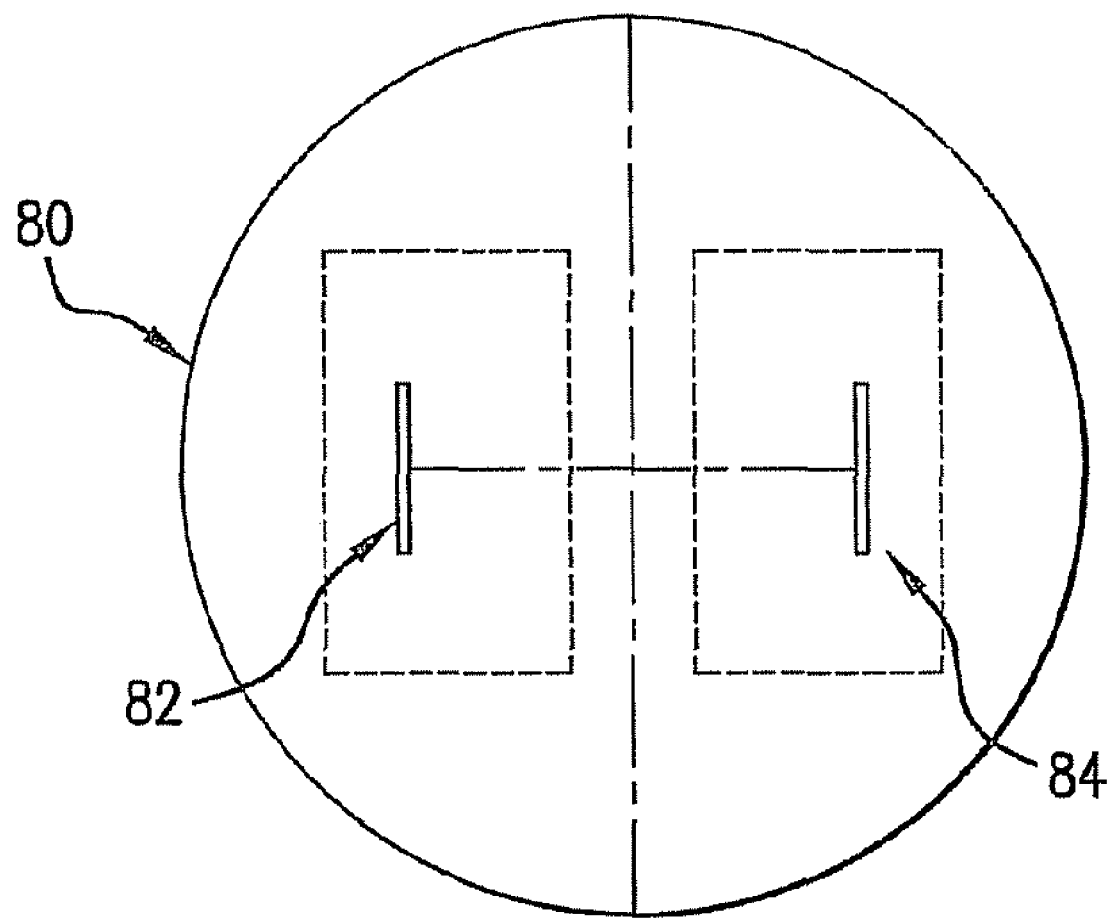
FIG. 8 is a schematic diagram showing projections onto a primary mirror of the portion of a glass surface being imaged (the object) and the linescan camera which records the image (linescan sensor), as well as the first and second portions of the primary mirror which form part of the optical path for scattered light from defects.

FIG. 8 illustrates the functioning of the primary mirror 80 in the reflective lenses of FIGS. 5-7. The small rectangles labeled as the "object" 82 and "linescan sensor" 84 show the area of the glass inspected and the area of the image sensor, respectively. As shown by the dashed rectangles (the first and second portions of the primary mirror 80), the footprint on the primary mirror 80 is much larger. As can be seen from an examination of this figure in combination with FIGS. 5-7, scattered light from the glass sheet (the object) reaches the linescan sensor by an optical path that includes reflection from the first portion of the concave primary mirror 5, reflection from the convex secondary mirror 6, and reflection from the second portion of the concave primary mirror 5. Although shown as rectangles in FIG. 8, the first and second portions will typically have kidney shaped configurations. See, for example, U.S. Pat. Nos. 3,951,546 and 7,158,215.

More particularly, the portion of the surface of the glass sheet that is in best focus in the image plane for the reflective lenses of the present disclosure has a curved (arcuate) shape with a radius substantially equal to the distance between the object and the centers of curvature of the mirrors. As discussed above, linescan cameras have a rectangular shape. In accordance with the present disclosure, it has been discovered that the image aberrations associated with this rectangular shape do not detract from the inspection system's ability to detect defects of the type encountered in the manufacture of glass sheets provided the radius of curvature R of the primary mirror, the lens' numerical aperture (NA), and the sensor's length L and width W satisfy the following relationships:

$L/R \leq 0.25$; and $W/R \leq 0.14*(\text{sqrt}(1-(L/R)^2)-1)+0.046$ for $NA \geq 0.10$; and $W/R \leq 0.14*(\text{sqrt}(1-(L/R)^2)-1)+0.033$ for $NA \geq 0.12$; and $W/R \leq 0.14*(\text{sqrt}(1-(L/R)^2)-1)+0.020$ for $NA \geq 0.15$.

Figure 9:
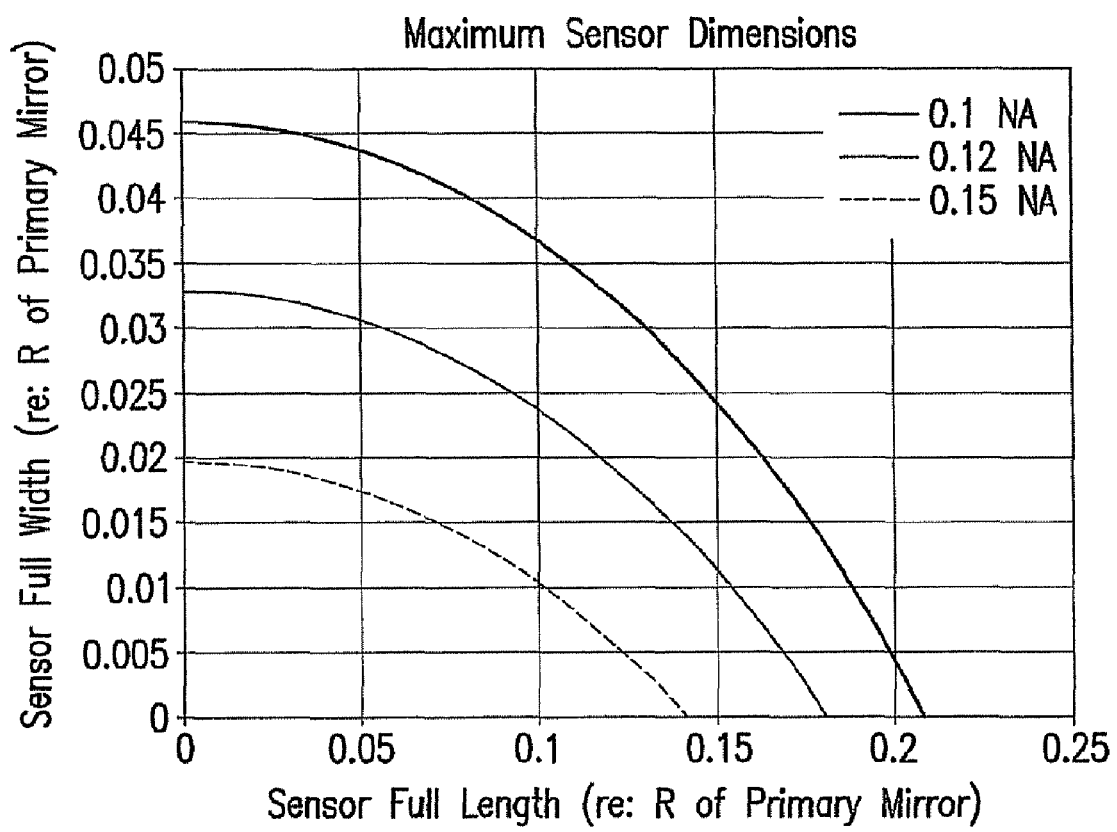
FIG. 9 is a plot showing the working ranges (areas under the curves) in terms of normalized length L and normalized width W of the linescan sensor (i.e., L/R and W/R where R is the radius of curvature of the primary mirror of the reflective lens) as a function of the reflective lens' numerical aperture (NA).

A plot of these relationships is shown in FIG. 9, where the horizontal axis shows the length L normalized to the radius of curvature of the primary mirror, i.e., L/R, and the vertical axis shows the width W again normalized to the radius of curvature of the primary mirror, i.e., W/R.

Figure 10:
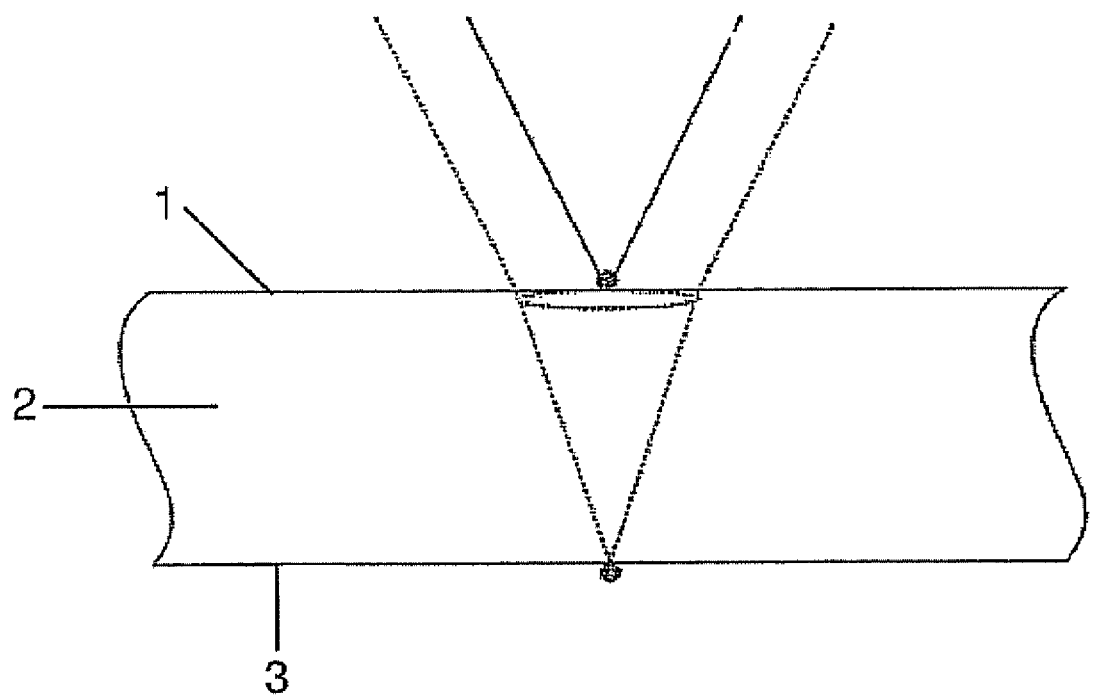
FIG. 10 is a schematic diagram illustrating the role of a lens' numerical aperture in keeping a desired surface of a glass sheet in-focus while keeping the sheet's other surface out-of focus.

FIG. 10 is a schematic diagram illustrating the role of the lens' numerical aperture in keeping a desired surface 1 of the glass sheet 2 in-focus while keeping the other surface 3 out-of focus. Keeping one surface 1 in focus and the other surface 3 out-of-focus is important when there are defects on more than one surface of the sheet 2, which is almost always the case. As the glass sheet 2 becomes thinner, and the distance between the surfaces decreases, it becomes increasingly difficult to distinguish defects on the different surfaces. Two aspects of the reflective lenses of the inspection systems disclosed herein allow defects to be accurately classified according to which surface they occur on.

Figure 11:
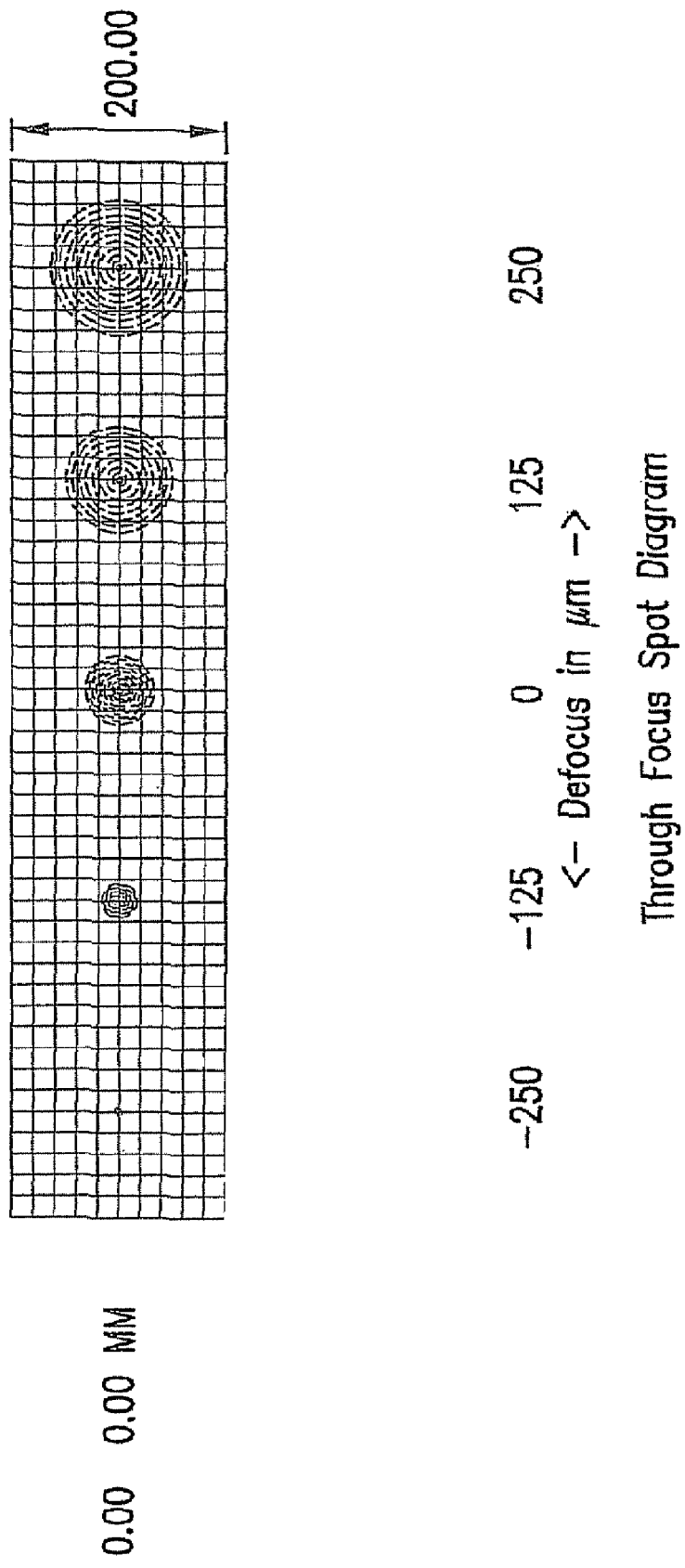
FIG. 11 is a ZEMAX plot illustrating the variation in point spread function from one surface of a glass sheet (the −250 micron point) to the other surface (the 250 micron point) for the telecentric reflective lens of FIG. 5.

First, the lens can be produced with a sufficient numerical aperture, which results in a sufficiently small depth of field, to allow the surface of interest 1 to be in-focus while putting the other surface 3 substantially out-of-focus. A numerical aperture of approximately 0.1 or higher is practical for achieving this result for glass sheets having thicknesses in the range of 0.2 to 1.2 millimeters. This difference between in-focus and out-of-focus behavior is illustrated in FIG. 11 which is a plot of the point spread function through focus for the reflective lens of FIG. 5 from one surface of a glass sheet (the −250 micron point) to the other surface 3 (the 250 micron point). In FIG. 11, the units are micrometers, Airy Radius is 2.714 micrometers, field is 1, RMS Radius is 23.021, GEO Radius is 31.909, the scale bar is 200, the reference is the chief ray, and the surface is IMA. As indicated in Table 1, the FIG. 5 lens has a numerical aperture of 0.12. The range of 0.5 mm was used in constructing this plot since it approximately corresponds to the optical thickness of a 0.7 mm thick glass sheet. Note that the defocused spot is ~0.12 mm in diameter, which is 200× larger in diameter than the in-focus spot and therefore $4 \times 10^4$ lower in irradiance. Even if the desired image is not in perfect focus, due to the mechanical handling of the sample (e.g., mechanical vibration of the sample), defects from the undesired side will appear much larger than those from the desired side.

More generally, to facilitate distinguishing defects on the first face from defects on the second face of a glass sheet, in certain embodiments, the optical system when focused on the first face has a point spread function of semi-diameter D1 at that face and has a point spread function of semi-diameter D2 at the second face, where D1 and D2 satisfy the relationship $D2/D1 \geq 35$. As shown in FIG. 11, the reflective lens of FIG. 5 fully satisfies this criterion.

Figure 12:
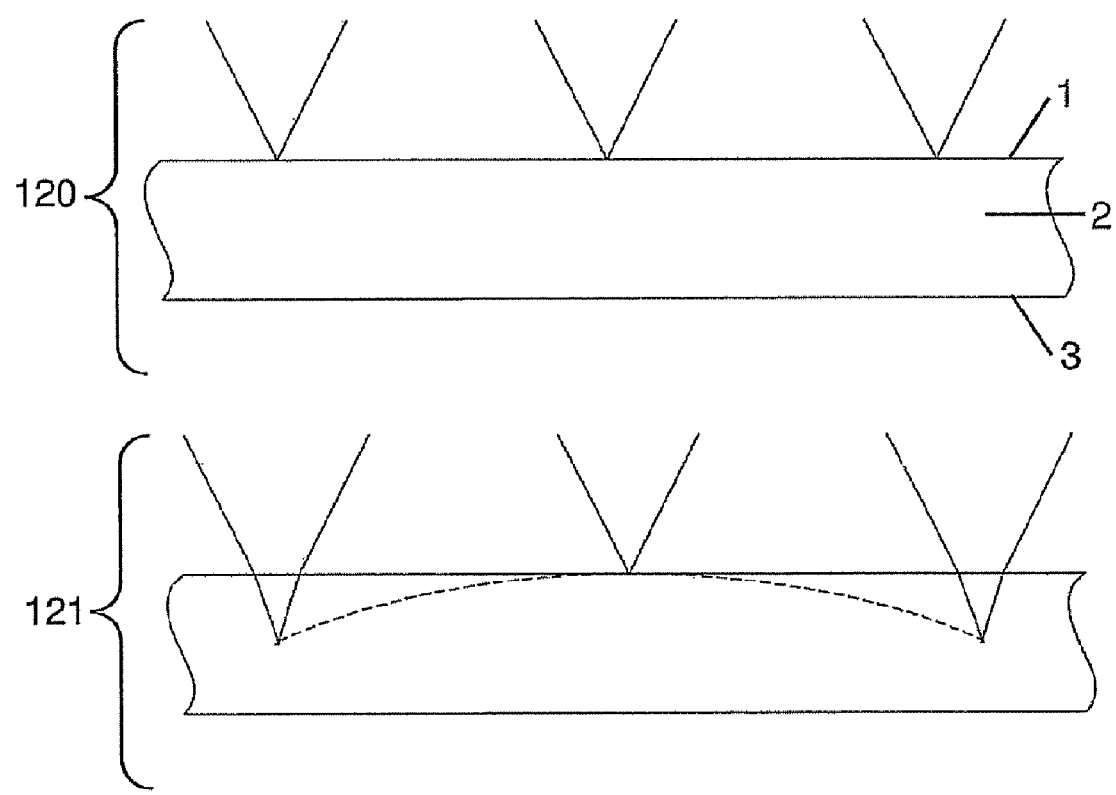
FIG. 12 is a schematic diagram illustrating the role of low field curvature in keeping a desired surface of a glass sheet in-focus while keeping the sheet's other surface out-of focus over a lens' entire field-of-view.

Second, the field of the lens is exactly flat along a circular arc, and substantially flat along a linear approximation to that circular arc. FIG. 12 illustrates the role a flat field 120, as opposed to a field having a large field curvature 121, plays in distinguishing defects on one surface 1 from those on the opposite surface 3. The combination of a large numerical aperture and a flat field 120 puts the surface of interest 1 in-focus while keeping the other surface 3 substantially out of focus over the entire field of view of the lens.

Figure 13:
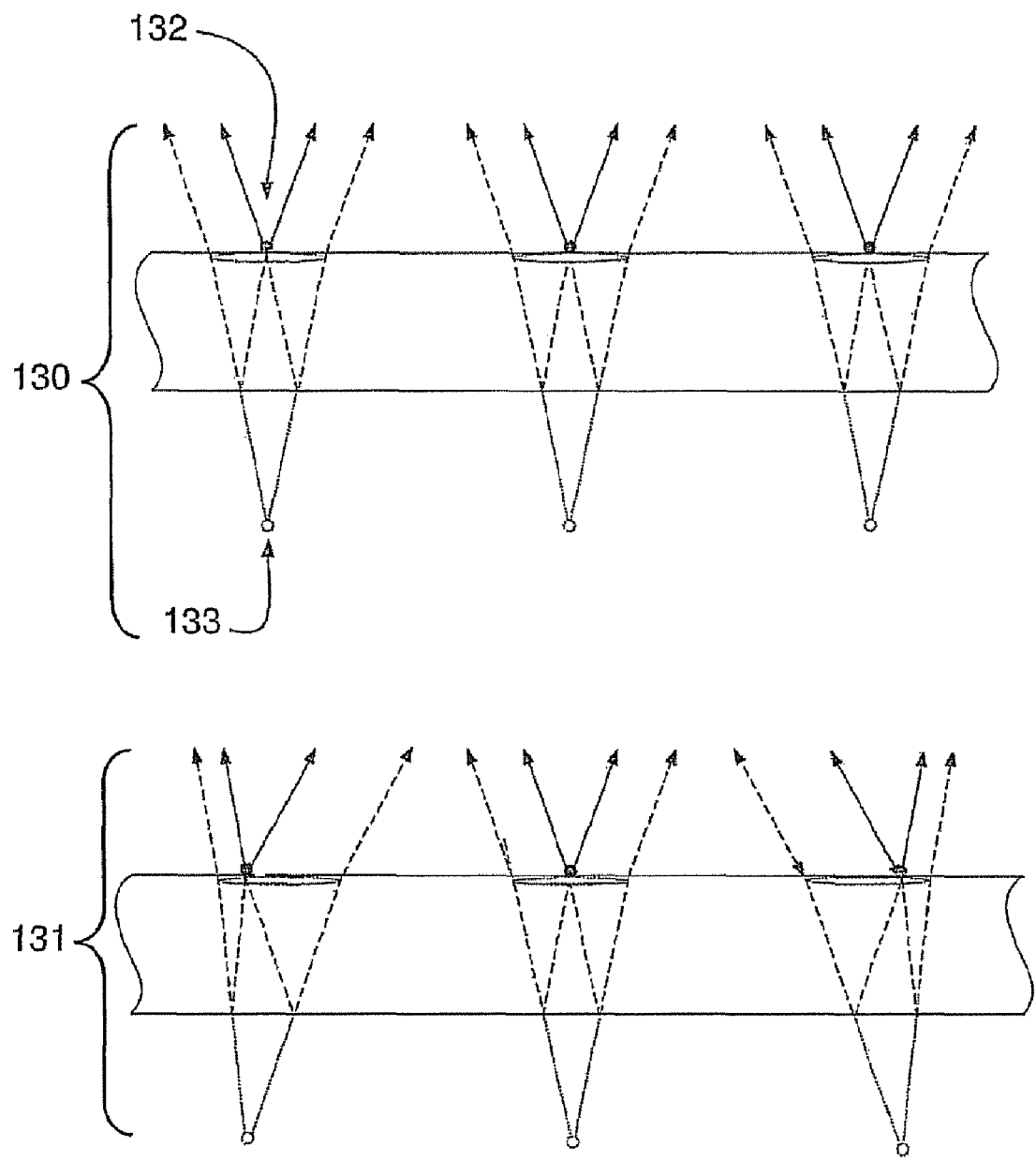
FIG. 13 is a schematic diagram illustrating an advantage of a substantially telecentric lens in maintaining consistency of detection geometry over the entire field of view.

FIG. 13 is a schematic diagram illustrating an advantage of a substantially telecentric configuration 130, versus a non-telecentric configuration 131, in maintaining consistency of detection geometry over the entire field of view. A system inspecting a transparent substrate with two or more partially reflective surfaces is subject to spurious or "ghost" images 133 of defects on one surface which scatter light that is then reflected by a different surface into the imaging system. These spurious images can alter the true image of a defect substantially. Indeed, they are often brighter than the true image. These ghost images can be separated from the true image by image processing techniques. However, if the relationship between ghost and true images varies across the field of view of the lens, this image processing task becomes more difficult.

If, however, the imaging system is telecentric or substantially telecentric, then the spatial relationship between the true and spurious images is fixed across the field of view, substantially reducing the image processing complexity. FIG. 13 illustrates this benefit of the reflective lenses of the present disclosure. Specifically, it shows how telecentricity or substantial telecentricity in object space maintains a consistent relationship over the field of view between the image 132 of a defect on the first surface and the ghost image 133 reflected by the second surface.

Figure 14:
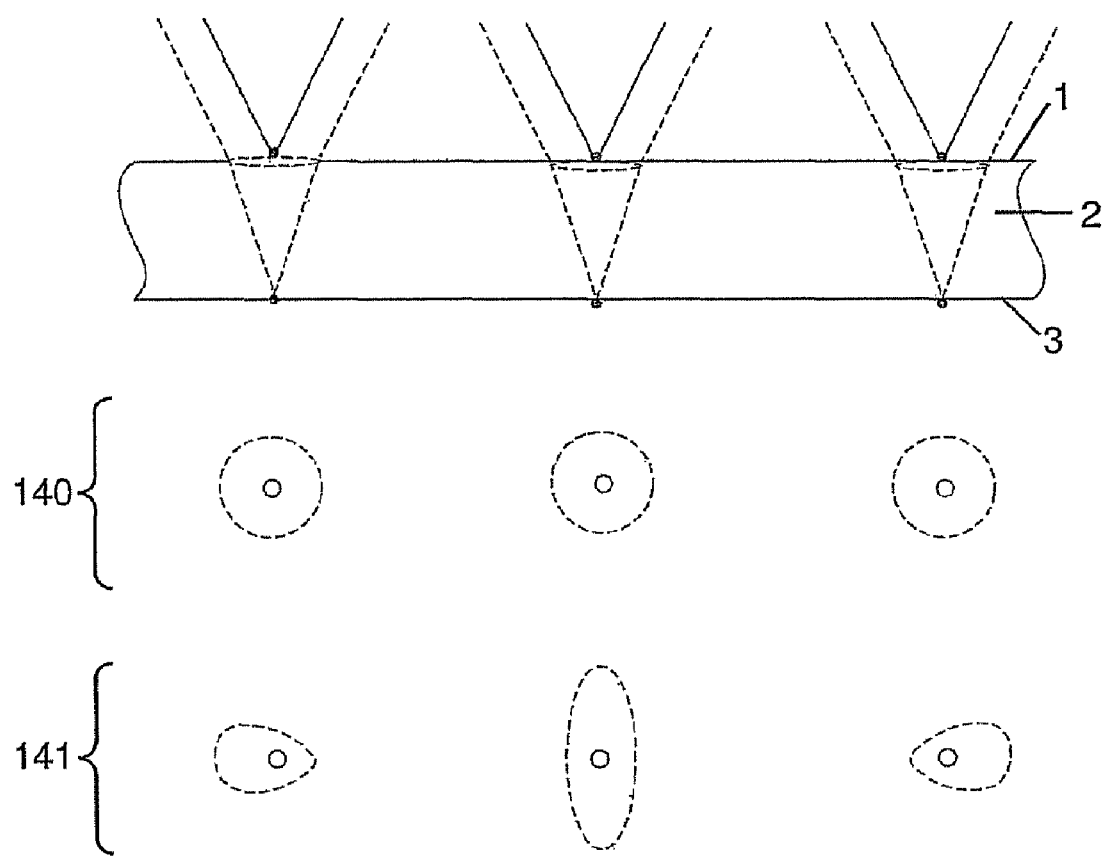
FIG. 14 is a schematic diagram illustrating an advantage of consistent image quality both in-focus and out-of-focus.

FIG. 14 illustrates the importance of a well-corrected image across the whole field of view, namely, consistent image quality 140 both in-focus and out-of-focus, as opposed to inconsistent image quality 141. As can be seen from this figure, in-focus and out-of-focus images that are consistent across the field of view assist in differentiating defects on the surface-of-interest from defects on the other surface 3. This is particularly important when applying image processing to extract features of interest. Such consistent image quality 140 obtains when the linescan camera has the dimensions described above.

The telecentricity or substantial telecentricity of the reflective lens is also of value in focusing. Thus, reducing the distance from the lens to the sensor has the effect of increasing the corresponding optical distance from the lens to the object, without changing the magnification or degrading the quality of the image, as long as this reduction is not too great. This is a result of the lens being telecentric or substantially telecentric on the image side as well as the object side, and arises from the symmetry of the lens design. Thus, in addition to focusing on the object side, focusing can also be accomplished by varying the effective path length between the lens and the sensor to compensate for varying distance from the lens to the object.

Figure 15:
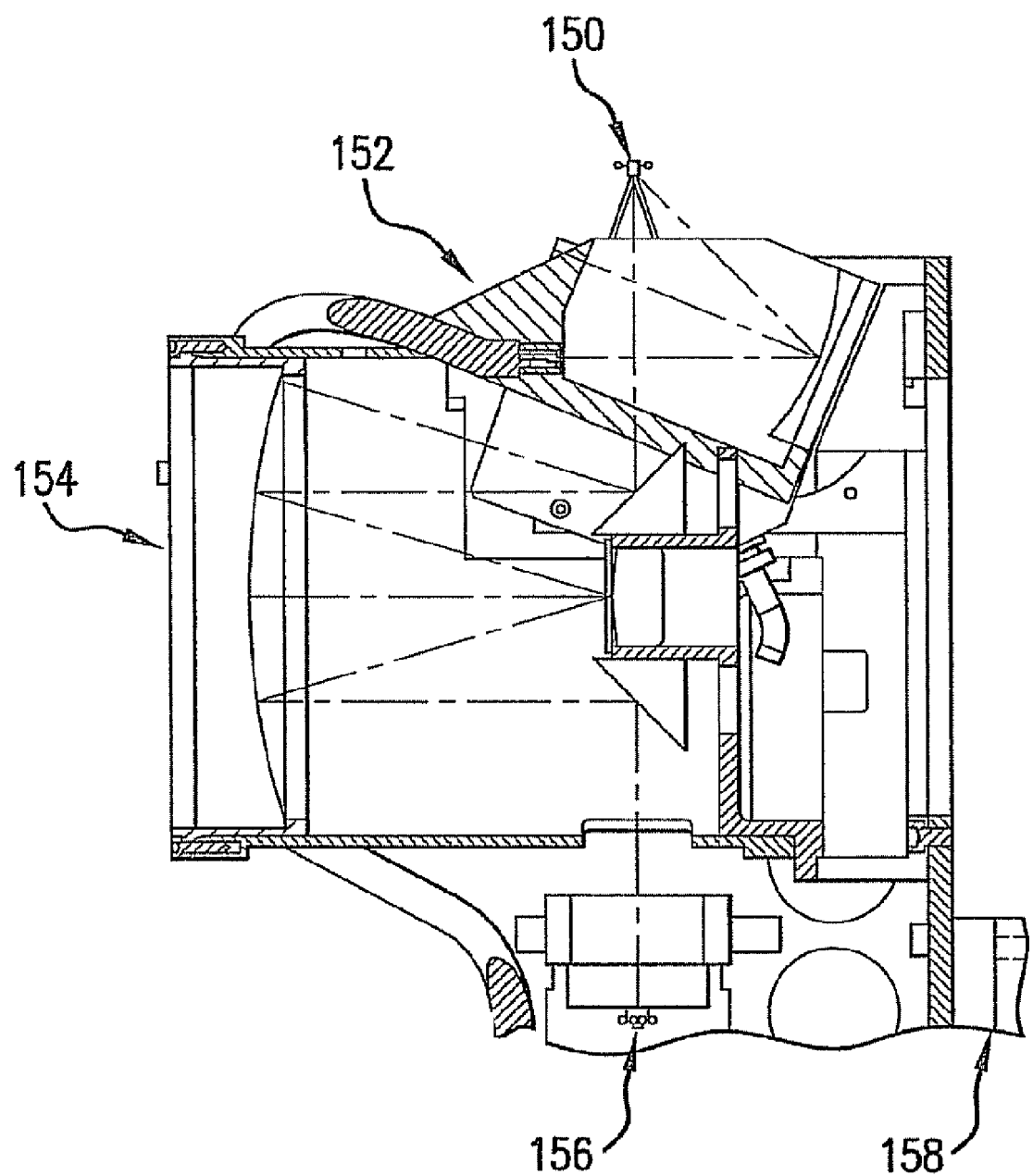
FIG. 15 illustrates representative packaging of an embodiment of an inspection system of the present disclosure.

FIG. 15 illustrates representative packaging of the components of an embodiment of the inspection system of the present disclosure, namely: a position 150 for the surface to be inspected; an illuminator 152; a position 156 for a linescan camera; and a focusing mechanism 158. The reflective lens 154 of this embodiment is that of FIG. 5. From Table 1, the diameter of the primary mirror of this lens is approximately 150 millimeters or about 6 inches. Accordingly, the entire inspection system can be provided in a very small package, e.g., a package having a volume on the order of 5,000 cubic centimeters or 300 cubic inches.

In addition to the ability to package the inspection system in a small package, because of its use of a reflective lens, the system can be produced at lower cost than existing inspection systems using refractive lenses. In particular, the reflective lens uses spherical elements which can be fabricated to cover a large field of view at low cost. Specifically, compared to refractive lenses, spherical mirrors are easy to fabricate and can be made from inexpensive materials. As a reflective lens, it is also color corrected at all wavelengths.

The disclosure thus provides systems for inspecting one or both surfaces of a glass sheet. The system is mounted so that the surface to be inspected is in the object plane of a reflective lens. The lens images a thin stripe area, long in the direction tangent to the lens circumference and short in the radial direction, onto a linescan camera with unity magnification. A line illuminator can be mounted so that it illuminates the stripe area. To perform the inspection, the system is moved with respect to the glass in the direction perpendicular to the long axis of the stripe, either by moving the system over the glass or by moving the glass while the system is fixed. Image information is collected by the linescan camera during this motion and assembled into an areal image. For some embodiments, depending on the application, adjustments can be made during image collection to ensure focus of the image onto the linescan sensor. For example, the location of the focus position can be sensed, either with an external sensor measuring the distance from the glass to the lens, or by processing the image from the linescan camera to determine how this distance should be adjusted to maintain focus.

A variety of modifications that do not depart from the scope and spirit of the invention will be evident to persons of ordinary skill in the art from the foregoing disclosure. The following claims are intended to cover the specific embodiments set forth herein as well as modifications, variations, and equivalents of those embodiments.

TABLE 1

|  | Large | Small |
| --- | --- | --- |
| Radius, Primary Mirror | 304.8 | 204.216 |
| Diameter, Primary Mirror | 152 | 127 |
| Radius, Secondary Mirror | 152.426 | 102.1 |
| Mirror Vertex Distance | 151.111 | 100.929 |
| Working Distance* | 152 | 102 |
| NA | 0.12 | 0.12 |
| FOV | 28 × 2 | 28 × 2 |

*"Working Distance" is the distance from the vertex of the secondary mirror to the object plane.

What is claimed is:

1. Apparatus for inspecting a transparent glass sheet having a first surface and a second surface, the apparatus comprising:
   (A) a light source which illuminates a portion of the glass sheet;
   (B) a linescan camera which detects light scattered from defects on or in the glass sheet, the linescan camera comprising a plurality of pixels which form a light sensitive area having a length L and a width W; and
   (C) an optical system that transfers scattered light from defects to the linescan camera, the optical system having a numerical aperture NA and comprising:
      (i) a primary concave mirror having a first portion and a second portion, the mirror having a radius of curvature R; and
      (ii) a convex secondary mirror;
   wherein:
      (a) scattered light from a defect reaches the linescan camera by an optical path that includes reflection from the first portion of the concave primary mirror, reflection from the convex secondary mirror, and reflection from the second portion of the concave primary mirror;
      (b) the centers of curvature of the primary and secondary mirrors are substantially coincident and the radius of the secondary mirror is substantially equal to one-half of the radius of the primary mirror; and
      (c) L, W, and R satisfy the relationships:

$L/R \leq 0.25$; and $W/R \leq 0.14*(\text{sqrt}(1-(L/R)^2)-1)+0.046$ for $NA \geq 0.10$; and $W/R \leq 0.14*(\text{sqrt}(1-(L/R)^2)-1)+0.033$ for $NA \geq 0.12$; and $W/R \leq 0.14*(\text{sqrt}(1-(L/R)^2)-1)+0.020$ for $NA \geq 0.15$.

2. The apparatus of claim 1 wherein the optical system when focused on the first surface of the glass sheet has a point spread function of semi-diameter D1 at that surface and has a point spread function of semi-diameter D2 at the second surface, where D1 and D2 satisfy the relationship:

$D2/D1 \geq 35$ for a glass sheet having a thickness in the range of 0.2 to 1.2 millimeters.

3. The apparatus of claim 1, wherein NA satisfies the relationship:

$$0.10 \leq NA \leq 0.15.$$

4. The apparatus of claim 1, wherein the optical system has 1:1 magnification.

5. The apparatus of claim 1, wherein the optical system's aperture stop is located at the secondary mirror.

6. The apparatus of claim 1, wherein the pixel size of the linescan camera is in the range of 5 to 20 microns.

7. The apparatus of claim 1, wherein the optical path includes only reflective optical surfaces.

8. The apparatus of claim 1, wherein the optical system is substantially telecentric in object space such that the variation in image size is less than the size of a pixel of the linescan camera over the optical system's depth of field.

9. The apparatus of claim 1, wherein the optical system's field curvature is less than the optical system's depth of field.

10. The apparatus of claim 1, wherein the optical system's geometric distortion is less than 1% over the length L of the light sensitive area of the linescan camera.

11. The apparatus of claim 1, further comprising a focusing mechanism which adjusts at least one of:
   (i) the optical path length between the glass sheet and the first portion of the primary concave mirror object; and
   (ii) the optical path length between the second portion of the primary concave mirror object and the linescan camera.

12. Apparatus for inspecting a transparent glass sheet having a first surface and a second surface, the apparatus comprising:
   (A) a light source which illuminates a portion of the glass sheet;
   (B) a linescan camera which detects light scattered from defects on or in the glass sheet, the linescan camera comprising a plurality of pixels which form a light sensitive area having a length L and a width W; and
   (C) an optical system that transfers scattered light from defects to the linescan camera, the optical system having a numerical aperture NA and comprising:
      (i) a primary concave mirror having a first portion and a second portion, the mirror having a radius of curvature R; and
      (ii) a convex secondary mirror;
   wherein:
      (a) scattered light from a defect reaches the linescan camera by an optical path that includes reflection from the first portion of the concave primary mirror, reflection from the convex secondary mirror, and reflection from the second portion of the concave primary mirror;
      (b) the centers of curvature of the primary and secondary mirrors are substantially coincident and the radius of the secondary mirror is substantially equal to one-half of the radius of the primary mirror; and
      (c) the optical system when focused on a first surface of the glass sheet has a point spread function of semi-diameter D1 at that surface and has a point spread function of semi-diameter D2 at the second surface, where D1 and D2 satisfy the relationship:

$$D2/D1 \geq 35$$

for a glass sheet having a thickness in the range of 0.2 to 1.2 millimeters.

13. A method of detecting a defect on or in a transparent glass sheet having a first surface and a second surface, the method comprising:
   (A) illuminating a portion of the glass sheet;
   (B) transferring light scattered by a defect from the glass sheet to a linescan camera using an optical system having a numerical aperture NA and comprising:
      (i) a primary concave mirror having a first portion and a second portion, the mirror having a radius of curvature R; and
      (ii) a convex secondary mirror; and
   (C) providing relative motion between the glass sheet and the linescan camera;
   wherein:
      (a) scattered light from a defect reaches the linescan camera by an optical path that includes reflection from the first portion of the concave primary mirror, reflection from the convex secondary mirror, and reflection from the second portion of the concave primary mirror;
      (b) the centers of curvature of the primary and secondary mirrors are substantially coincident and the radius of the secondary mirror is substantially equal to one-half of the radius of the primary mirror;
      (c) the linescan camera comprises a plurality of pixels which form a light sensitive area having a length L and a width W; and
      (d) L, W, and R satisfy the relationships:

$$L/R \leq 0.25; \text{ and}$$

$$W/R \leq 0.14*(\text{sqrt}(1-(L/R)^2)-1)+0.046 \text{ for } NA \geq 0.10; \text{ and}$$

$$W/R \leq 0.14*(\text{sqrt}(1-(L/R)^2)-1)+0.033 \text{ for } NA \geq 0.12; \text{ and}$$

$$W/R \leq 0.14*(\text{sqrt}(1-(L/R)^2)-1)+0.020 \text{ for } NA \geq 0.15.$$

14. The method of claim 13 wherein the optical system when focused on the first surface of the glass sheet has a point spread function of semi-diameter D1 at that surface and has a point spread function of semi-diameter D2 at the second surface, where D1 and D2 satisfy the relationship:

$$D2/D1 \geq 35$$

for a glass sheet having a thickness in the range of 0.2 to 1.2 millimeters.

15. The method of claim 13 further comprising focusing an image of the glass sheet on the linescan camera by adjusting at least one of:
   (i) the optical path length between the glass sheet and the first portion of the primary concave mirror; and
   (ii) the optical path length between the second portion of the primary concave mirror and the linescan camera.

16. The method of claim 13 wherein the optical system is substantially telecentric in object space such that the variation in image size is less than the size of a pixel of the linescan camera over the optical system's depth of field.

17. The method of claim 13 wherein the optical system's field curvature is less than the optical system's depth of field.

18. The method of claim 13 wherein the optical system's geometric distortion is less than 1% over the length of the light sensitive area of the linescan camera.

19. A method of producing a glass sheet, comprising: obtaining a glass sheet; and detecting defects in the glass sheet according to the method of claim 13.

* * * * *